United States Patent [19]

Mansfield

[11] Patent Number: 4,481,092

[45] Date of Patent: Nov. 6, 1984

[54] PHOTO-INITIATED EPOXIDATION OF ALLYL CHLORIDE

[75] Inventor: Kevin T. Mansfield, North Kingston, R.I.

[73] Assignee: Ciba-Geigy Corporation, Ardsley, N.Y.

[21] Appl. No.: 502,384

[22] Filed: Jun. 8, 1983

Related U.S. Application Data

[63] Continuation-in-part of Ser. No. 450,814, Dec. 20, 1982, abandoned.

[51] Int. Cl.$^3$ ............................................. B01J 19/12
[52] U.S. Cl. .......................... 204/158 R; 204/162 R
[58] Field of Search ....................... 204/158 R, 162 R

[56] References Cited

U.S. PATENT DOCUMENTS 4,383,904 5/1983 Shepherd.

OTHER PUBLICATIONS

S. J. Cristol et al., J. Am. Chem. Soc., 91, 7554, (1969).
S. J. Cristol et al., J. Am. Chem. Soc., 95, 7067 (1973).
N. Shimizu and P. D. Bartlett, J. Am. Chem. Soc., 98:14, 4193, (1976).
P. D. Bartlett and J. Becherer, Tetrahedron Letters, 33, 2983, (1978).
C. S. Foote, Acc. Chem. Res., 1, 104, (1968).
T. Sasaki, J. Am. Chem. Soc., 103:13, 3882, (1981).
J. P. Shepherd, J. Org. Chem., 48, 337, (1983).

*Primary Examiner*—Howard S. Williams
*Attorney, Agent, or Firm*—Luther A. R. Hall

[57] ABSTRACT

Epichlorohydrin is prepared by the epoxidation of allyl chloride by a process which comprises irradiating an oxygen-saturated solution of allyl chloride in an aprotic solvent in the presence of an effective amount of an alpha-diketone sensitizer with the radiation of a 450 watt medium-pressure mercury lamp. Propylene oxide is prepared by a similar process by the epoxidation of propylene.

5 Claims, No Drawings

PHOTO-INITIATED EPOXIDATION OF ALLYL CHLORIDE

This is a continuation-in-part of application Ser. No. 450,814, filed Dec. 20, 1982, now abandoned.

FIELD OF THE INVENTION

This invention relates to the photooxidation of allyl chloride and of propylene, and more particularly to their photooxidation to epichlorohydrin and propylene oxide respectively.

BACKGROUND OF THE INVENTION

Dye-sensitized photooxidation has been extensively investigated, but has not been suggested as useful for the oxidation of simple olefins to the corresponding epoxides.

P. D. Bartlett and coworkers (J. Am. Chem. Soc., 98:14, 4193 (1976) and Tetrahedron Letters, 33, 2983 (1978)) have investigated the photooxidation of aryl olefins and cycloaliphatic olefins. They report that, while epoxidation occurs with alpha-diketone sensitizers, there is often substantial to complete destruction of the sensitizer. From their studies it is clear that the photooxidation of simple olefins was not believed possible or feasible.

Dye-sensitized photooxidation reactions of olefins have also been investigated by C. S. Foote (Acc. Chem Res, 1, 104 (1968)). Under most conditions, the predominant oxidation products from olefins containing allylic hydrogen atoms are the corresponding hydroperoxides. But as found by Bartlett et al (supra) photooxidation of highly substituted or hindered olefins in the presence of alpha-diketones often affords moderate to high yields of the corresponding epoxides.

T. Sasaki (J. Am. Chem. Soc., 103:13, 3882 (1981)) succeeded in preparing propylene oxide via the photochemical oxidation of propylene with oxygen in acetonitrile in the presence of sulfur dioxide. The reaction appears to proceed via a sulfur dioxide charge transfer complex completely unrelated to the instant invention and gives as a major product poly(propylene sulfonate). Sasaki specifically states that "propylene oxide is not very stable under the reaction conditions and is gradually converted to some polymeric products". He further observes that, "epoxide formation cannot be observed in solvents with ionization potentials lower than ca. 9.5 eV and/or dielectric constants smaller than ca. 10". More specifically "propylene oxide cannot be obtained in solvents such as benzene ... (and) ... dichloromethane", among others.

J. P. Shepherd, J. Org. Chem. 48, 337 (1983), describes the photoepoxidation of propylene at elevated pressures when sensitized by alpha-diketones to yield propylene oxide.

Epichlorohydrin is a crucial raw material used in the high volume manufacture of components of epoxy resins. The present commercial methods for the manufacture of epichlorohydrin require the use of relatively strong oxidizing agents such as hydroperoxides, hypohalites, and the like. The utilization of these oxidizers requires costly technology to enable the safe handling and regeneration of the oxidizing agent as well as expensive treatment of the resulting by-products.

Propylene oxide (methyloxirane) is another important commercial intermediate. It is used in the preparation of polyethers and ultimately polyurethanes, as well as in the preparation of propylene glycols. Propylene oxide, too, requires the use of strong oxidizers for commercial manufacture.

A direct oxidation method using air or oxygen as the oxygen source and a direct oxidation agent would have a great impact on the existing technology with concomitant economic benefits.

OBJECTS OF THE INVENTION

It is the primary object of this invention to provide a method for direct photo-initiated epoxidation of allyl chloride or of propylene as a means of producing epichlorohydrin or propylene oxide respectively.

This, ancillary and/or related objects are attained by the present invention as described and detailed below.

THE INVENTION

Compounds contemplated as suitable for conversion to their corresponding epoxides by the instant invention conform to the general formula $$R_1-CH_2-CH=CH_2 \text{ or}$$

$$R_2(CH_2-CH=CH_2)_n$$

where
$R_1$ can be hydrogen or an alkyl, aralkyl or aryl hydrocarbyl residue such as methyl, ethyl, propyl, benzyl, phenyl; various branched-chain hydrocarbyl or substituted aralkyl or aryl residues; halogen, hydroxy, esters or ethers derived from aliphatic alcohols, monophenols such as phenol, o-cresol or p-tert-butylphenol, and $R_2$ is an n-valent residue from a polyether derived from bisphenol A (2,2-bis(4-hydroxyphenyl)propane), bisphenol F (4,4'-methylenediphenol), a phenol novolac or a cresol novolac where n is 2 to 10.

This invention is particularly focused on the discovery that allyl chloride or propylene is converted to epichlorohydrin or propylene oxide respectively via the irradiation by medium pressure mercury lamps of an oxygen-saturated aprotic solvent solution of the starting unsaturated compound using an alpha-diketone as sensitizer.

More particularly, the instant invention pertains to a method for the preparation of epichlorohydrin by the epoxidation of allyl chloride which comprises irradiating with the radiation of a 450 watt medium-pressure mercury lamp an oxygen-saturated solution of allyl chloride in an aprotic solvent in the presence of an effective amount of an alpha-diketone sensitizer for sufficient time to effect epoxidation of the allyl chloride to epichlorohydrin; or to a method for the preparation of propylene oxide by the epoxidation of propylene which comprises irradiating with the radiation of a 450 watt medium-pressure mercury lamp an oxygen-saturated solution of propylene in an aprotic solvent in the presence of an effective amount of an alpha-diketone sensitizer for sufficient time to effect epoxidation of the propylene to propylene oxide.

The alpha-diketone sensitizers useful in the instant invention are biacetyl, benzil, 1-phenyl-1,2-propanedione, or mixtures thereof. Other alpha-diketones absorbing light in the same region of the UV and visible spectra would be expected to perform satisfactorily as well. The preferred sensitizer is biacetyl or benzil.

The amount of alpha-diketone sensitizer used in the instant invention is that amount which is effective to cause the epoxidation to occur under the conditions of the instant process. Normally essentially equimolar amounts of the alpha-diketone sensitizer, compared to the allyl chloride or propylene being epoxidized, are employed, but from 0.3 to 2 molar equivalent of alpha-diketone sensitizer per mole of allyl chloride or propylene may be used satisfactorily in the instant process.

Aprotic solvents suitable for the instant invention include aliphatic hydrocarbons such as the various pentanes, hexanes, cyclohexane, heptanes, methylcyclohexane, octanes, etc; aromatic hydrocarbons such as benzene, toluene, ethylbenzene, xylene and various chlorinated derivatives thereof; chlorinated hydrocarbons such as methylene chloride, chloroform, carbon tetrachloride; ethers such as diethyl ether, tetrahydrofuran and dioxane; esters such as ethyl acetate, nitriles such as acetonitrile and propionitrile and other aprotic dipolar solvents such as nitromethane.

The aprotic solvents found especially useful in the instant process are benzene or methylene chloride. Methylene chloride was particularly preferred in the process to prepare epichlorohydrin from allyl chloride since this epoxidation reaction exhibited more selectivity in methylene chloride than in benzene.

In the preparation of propylene oxide from propylene, benzene was the preferred aprotic solvent.

The radiation is carried out at wave lengths obtained from 450 watt medium-pressure mercury lamps. The oxygen-saturated benzene or methylene chloride solutions of the olefins are conveniently maintained at temperatures up to about 30° C., and preferably in the range 20°–26° C., while continuously saturating the reaction mixture with gaseous oxygen. Preferably, the gaseous oxygen source is pressurized air.

While the reactions are conveniently conducted at about atmospheric pressure in the laboratory, running the reactions at elevated pressures to increase the solubility of the gaseous reactants in the solvent would be expected to increase the reaction rate.

DETAILED DESCRIPTION OF THE INVENTION

The photooxidations are preferably performed in a jacketed photolysis apparatus. The radiation source is at least one 450 watt medium-pressure mercury lamp such as manufactured by Hanovia. A pyrex shield is used to filter out light of wavelength less than 318 nm which causes undesired secondary reactions to occur.

It should be noted that the medium-pressure mercury lamps operating at about 450 watts of Hanovia are preferred. Tungsten-iodine 650 watt lamps such as manufactured by General Electric (DWY) and a commercial "GE Sunlamp" were not satisfactory light sources. All attempts to epoxidize the olefins using these light sources were unsuccessful.

The preferred sensitizers for the process of this invention are alpha-diketones such as biacetyl, benzil and 1-phenyl-1,2-propanedione. Specifically biacetyl (2,3-butanedione) and benzil (diphenylethanedione) are preferred. Other common photooxidation sensitizers such as the dyes Methylene Blue; Bengal Red B; Tetraphenylporphine; polymer-bound Rose Bengal, as well as benzophenone, all fail to promote the desired epoxidations.

The photooxidation of alkyl chloride to epichlorohydrin proceeds according to the following scheme:

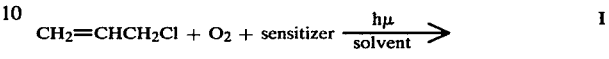

allyl chloride

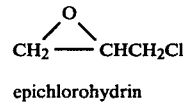

epichlorohydrin

The photooxidation of propylene to propylene oxide proceeds according to the following scheme:

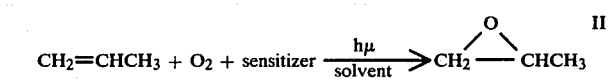

propylene        propylene oxide

The preparation of both epichlorohydrin and propylene oxide according to the preferred schemes of equations I and II is described in the appended examples.

The alpha-diketone sensitizers and olefins used in the instant process are items of commerce.

EXAMPLE 1

Preparation of Epichlorohydrin

A solution of 11.3 grams (0.148 mole) allyl chloride and 12.6 grams (0.147 mole) of biacetyl in 400 ml benzene (or methylene chloride) was charged into a 700 ml capacity photolysis apparatus equipped with water-cooling and having a Hanovia 450 watt medium-pressure mercury lamp, radiation source, and surrounded by a pyrex shield. The jacket cooling water was turned on and oxygen, introduced via a fritted glass filter stick, was bubbled through the vigorously stirred mixture. The solution was irradiated by the Hanovia lamp. The temperature of the mixture was maintained in the range 20°–26° C.

The progress of the reaction was followed by removing an aliquot of the reaction mixture for analysis by gas chromotography. The reaction mixtures generally yielded positive starch-iodide tests suggesting the presence of allyl hydroperoxides.

Table 1 shows several runs (a)–(g) according to Example 1 with variations of irradiation time, reaction solvent, and sensitizer.

TABLE 1

PHOTOCHEMICAL OXIDATION OF ALLYL CHLORIDE TO EPICHLOROHYDRIN (EPI) USING MEDIUM-PRESSURE MERCURY LAMP

| Run # Example 1 | SENSITIZER | SOLVENT | IRRADIATION TIME | GC ANALYSIS[1] ALLYL CHLORIDE | EPI | UNKNOWNS | EST. YIELD EPI |
|---|---|---|---|---|---|---|---|
| Run a | Benzil | $CH_2Cl_2$ | 0 Min. | 6.70% | N.D.[2] | 0.40% | 0.0% |
| Run b | Benzil | $CH_2Cl_2$ | 15 Min. | 6.60% | N.D.[2] | 0.40% | 0.0% |
| Run c | Benzil | $CH_2Cl_2$ | 55 Min. | 6.40% | 0.03% | 0.41% | 0.5% |
| Run d | Biacetyl | Benzene | 35 Min. | 1.00% | 0.013% | 0.02% | 1.3% |
| Run e | Biacetyl | Benzene | 1 Hr. 15 Min. | 0.85% | 0.017% | 0.24% | 1.7% |

TABLE 1-continued
PHOTOCHEMICAL OXIDATION OF ALLYL CHLORIDE TO EPICHLOROHYDRIN (EPI) USING MEDIUM-PRESSURE MERCURY LAMP

| Run # Example 1 | SENSITIZER | SOLVENT | IRRADIATION TIME | GC ANALYSIS[1] ALLYL CHLORIDE | EPI | UNKNOWNS | EST. YIELD EPI |
|---|---|---|---|---|---|---|---|
| Run f | Biacetyl | Benzene | 4 Hr. 5 Min. | 0.34% | 0.027% | 0.40% | 2.7% |
| Run g | Benzil | Benzene | 1 Hr. 0 Min. | 1.20% | 0.010% | 0.08% | 0.8% |
| Run h | Benzil | Benzene | 6 Hr. 45 Min. | 1.00% | 0.032% | 0.15% | 2.7% |
| Run i[3] | Biacetyl | Benzene | 1 Hr. 45 Min. | 37.30% | 0.05% | 0.08% | 0.1% |
| Run j[4] | Biacetyl | Benzene | 2 Hr. 45 Min. | 32.10% | 0.05% | 2.10% | 0.1% |

[1]Gas chromatographic (GC) analyses are area percent.
[2]N.D. = none detected
[3]Allyl chloride/benzene ratio = 2.45 (wt/wt); 6 mole percent biacetyl charged.
[4]Acetic acid added to sample i, then mixture irradiation continued as Run j, to form peracetic acid in situ.

Gas chromotography analysis (area percent) indicated that epichlorohydrin was formed in a yield of about 3%, accompanied by a several unknown compounds. The use of methylene chloride as the solvent medium afforded a cleaner conversion, 0.5% to 1.0% yield of epichlorohydrin in one hour accompanied by only two unknown by-products.

EXAMPLE 2
Preparation of Propylene Oxide

A solution of 31.1 grams (0.148 mole) benzil in 400 ml benzene was charged to the photolysis apparatus described in Example 1. Propylene was bubbled through the stirred solution via a fritted glass filter stick for approximately twenty minutes. The jacket cooling water was turned on and oxygen or an oxygen-propylene mixture was bubbled through the same fritted gas stick. The solution was irradiated with the Hanovia medium-pressure mercury lamp, maintaining the vessel temperature between 20°–26° C. The reaction was followed by periodically removing an aliquot of the reaction mixture for gas chromotographic analysis.

Table 2 summarizes the results obtained with several runs, 2(a)–2(l), according to Example 2.

The epoxidation of propylene proceeded very cleanly as compared to the epoxidation of allyl chloride. The selectively of the reaction was excellent despite the modest yield. Propylene was converted cleanly to propylene oxide in about 10% yield in one hour at about room temperature.

TABLE 2
PHOTOCHEMICAL OXIDATION OF PROPYLENE USING MEDIUM PRESSURE MERCURY LAMP

| Run # Example 2 | SENSITIZER | SOLVENT | IRRADIATION TIME | GC ANALYSIS[1] PROPYLENE | PROPYLENE OXIDE | EST. YIELD PROPYLENE OXIDE |
|---|---|---|---|---|---|---|
| Run a | Biacetyl | Benzene | 0 Min. | 1.41% | 0.000% | — |
| Run b | Biacetyl | Benzene | 15 Min. | 0.45% | 0.042% | 3.0% |
| Run c | Biacetyl | Benzene | 35 Min. | 0.03% | 0.100% | 7.1% |
| Run d | Biacetyl | Benzene | 18 Min. | 0.43% | N.D.[4] | — |
| Run e | Biacetyl | Benzene | 60 Min. | 0.23% | 0.110% | 7.9% |
| Run f | Benzil | Benzene | 0 Min. | 1.42% | N.D.[4] | — |
| Run g | Benzil | Benzene | 60 Min. | 0.34% | 0.050% | 3.5% |
| Run h[2] | Biacetyl | Benzene | 0 Min. | 1.70% | N.D.[4] | — |
| Run i[3] | Biacetyl | Benzene | 30 Min. | 1.00% | 0.040% | 2.3% |
| Run j | Biacetyl | Benzene | 0 Min. | 1.28% | N.D.[4] | — |
| Run k[3] | Biacetyl | Benzene | 15 Min. | 0.67% | 0.030% | 2.3% |
| Run l[3] | Biacetyl | Benzene | 120 Min. | 1.01% | 0.120% | 9.4% |

[1]Gas Chromatographic (GC) analyses are area percent.
[2]Acetic acid added to reaction to form peracetic acid in situ.
[3]Reaction mixture first saturated with propylene, then propylene and oxygen are bubbled simultaneously through solution while mixture was irradiated.
[4]N.D. = none detected.

The invention has been described according to its preferred modes, but art-recognized variations in materials and equipment are contemplated as within the scope of this invention. Such equivalents are intended to be within the scope of the appended claims.

What is claimed is:

1. A method for the preparation of epichlorohydrin by the epoxidation of allyl chloride which comprises irradiating with the radiation of a 450 watt medium-pressure mercury lamp an oxygen-saturated solution of allyl chloride in an aprotic solvent in the presence of an effective amount of an alpha-diketone sensitizer for sufficient time to effect epoxidation of the allyl chloride to epichlorohydrin.

2. A method according to claim 1 wherein the alpha-diketone sensitizer is biacetyl, benzil or 1-phenyl-1,2-propanedione.

3. A method according to claim 2 wherein the alpha-diketone sensitizer is biacetyl or benzil.

4. A method according to claim 1 wherein the aprotic solvent is benzene or methylene chloride.

5. A method according to claim 4 wherein the aprotic solvent is methylene chloride.

* * * * *